(12) United States Patent
Shtalryd

(10) Patent No.: US 10,098,594 B2
(45) Date of Patent: Oct. 16, 2018

(54) PORTABLE MONITORING DEVICE, SYSTEM AND METHOD FOR MONITORING AN INDIVIDUAL

(71) Applicant: Hisense Ltd, Rishon le Zion (IL)

(72) Inventor: Yaniv Shtalryd, Ness Ziona (IL)

(73) Assignee: HISENSE LTD, Rishon le Zion (IL)

( * ) Notice: Subject to any disclaimer, the term of this patent is extended or adjusted under 35 U.S.C. 154(b) by 71 days.

(21) Appl. No.: 15/202,386

(22) Filed: Jul. 5, 2016

(65) Prior Publication Data

US 2017/0000425 A1    Jan. 5, 2017

Related U.S. Application Data

(60) Provisional application No. 62/187,919, filed on Jul. 2, 2015.

(51) Int. Cl.
| | |
|---|---|
| *A61B 5/00* | (2006.01) |
| *A61B 5/0205* | (2006.01) |
| *A61B 5/021* | (2006.01) |
| *A61B 5/024* | (2006.01) |
| *A61B 5/113* | (2006.01) |

(52) U.S. Cl.
CPC ............ *A61B 5/746* (2013.01); *A61B 5/0017* (2013.01); *A61B 5/0026* (2013.01); *A61B 5/0205* (2013.01); *A61B 5/6803* (2013.01); *A61B 5/6804* (2013.01); *A61B 5/6892* (2013.01); *A61B 5/021* (2013.01); *A61B 5/02438* (2013.01); *A61B 5/113* (2013.01); *A61B 2560/0456* (2013.01)

(58) Field of Classification Search
None
See application file for complete search history.

(56) References Cited

U.S. PATENT DOCUMENTS

| | | | | |
|---|---|---|---|---|
| 2004/0147818 | A1* | 7/2004 | Levy ................. | A61B 5/02055 600/300 |
| 2008/0300499 | A1* | 12/2008 | Strube .................... | A61B 5/113 600/527 |
| 2014/0197946 | A1* | 7/2014 | Park ....................... | G08B 21/18 340/539.11 |

FOREIGN PATENT DOCUMENTS

JP             10-295695 A        11/1998

* cited by examiner

*Primary Examiner* — Muhammad N Edun
*Assistant Examiner* — Jerold Murphy
(74) *Attorney, Agent, or Firm* — Knobbe, Martens, Olson & Bear, LLP

(57) ABSTRACT

In some embodiments, a portable monitoring device for monitoring at least one physical parameter of an individual includes: a first sensor unit having a sensor for sensing the physical parameter of the individual; a control unit configured for receiving data from the first sensor unit and also from at least one other remote second sensor unit, identifying sensing mode of each of the first and second sensor units, and processing the received data; a carrying mechanism for having the portable device carried by the individual to be monitored; and one or more output devices for outputting indication and/or information associated with the processed data. The control unit can be configured for processing signal data of the first sensor unit or the remote second sensor unit, according to the identified sensing modes thereof.

26 Claims, 5 Drawing Sheets

PORTABLE MONITORING DEVICE, SYSTEM AND METHOD FOR MONITORING AN INDIVIDUAL

CROSS-REFERENCE TO RELATED APPLICATIONS

This application claims priority of U.S. provisional patent application No. 62/187,919, filed on Jul. 2, 2015 and incorporated herein by reference.

TECHNICAL FIELD

The present disclosure generally relates to devices, apparatuses, systems and methods for monitoring one or more primary vital signs for an individual such as, yet not limited to, respiration and/or pulse and the like.

BACKGROUND

Baby monitoring devices and systems for detection of respiratory failures such as apnea are widespread and typically use piezoelectric transducer sensors embedded in a plate that can be placed under the mattress of the baby bed for sensing respiratory thereof during sleeping. The sensor unit it usually connected via a data communication cable to a control unit which includes a processor for identification of alarming respiratory related situations such as apnea by identifying non-movement of the baby lying over the bed mattress over the sensor unit.

Other monitoring devices and systems are known in the art for monitoring the same and/or other vital signs related parameters such as pulse and/or blood pressure using the same type of sensors or other sensing technologies.

Patent no. EP0514744 by Shtalryd teaches such a system for monitoring respiratory behavior for detecting apnea and outputting an alarm upon detection of breathing cessations using a transducer movement detector.

US patent application publication no. 2008300499 teaches non-invasive monitoring devices for monitoring minute movements made by the body to report the presence or absence of respiration and normal heart rate. The movements being measured are the pulsations made by the normal operation of both the heart and lungs. This is done by converting the body movements into electrical signals with an adapted polymorph-piezoelectric transducer. The electrical signal that is detected is a mixed signal, a signal composed of a lower frequency (breathing contraction) and the higher frequency (heart pulse). The signals are detected by separating the body motions by an adaptive filter that has a break frequency at twice the frequency of the larger body movement signal (breathing contraction). The separate body movement signals operate with associated logic circuitry to allow each signal to be independently measured, recorded, and acted upon to determine if the individual (patient) is undergoing a life threatening experience. Such an event by either signal will trigger an audio and visual display alarm which is attached on or near the patient. The alarm event trigger is also connected to a low voltage detector circuit to indicate that the supply voltage has dropped below an acceptable level.

Patent application no. JPH10295695 teaches a pressure sensing type respiration and body movement sensor, which detests the respiratory movement and the body movement caused by change in pressure applied on the sensor, generally arranged under the breast of a testee in bed. The sound sensor detects the respiration sound such as a snore and is constituted for example, a microphone and a sound conditioner. The recorder which records data obtained from the respiration and body movement sensor and the sound sensor prints or displays the data recorded in a magnetic storage medium or an electric record medium on a display, etc., by a data processing device during or after recording so as to enable the confirmation.

SUMMARY

The present disclosure provides embodiments of a portable monitoring device for monitoring at least one physical parameter of an individual such as respiratory behavior, pulse and the like, the portable monitoring device comprising: a power source; a first sensor unit having at least one sensor for sensing at least one physical parameter of the individual; a control unit configured for receiving output signal data from the first sensor unit and from at least one other remote second sensor unit having at least one sensor for monitoring at least one physical parameter, identifying sensing mode of each of the first and second sensor units, and for processing data received from the first and/or second sensor unit; a carrying mechanism for having the portable monitoring device carried by the individual to be monitored, the control unit and the at least one first sensor being embedded in the carrying mechanism; and at least one output device for outputting indication and/or information associated with the processed first sensor and/or second sensor data, wherein the control unit is further configured for processing signal data of at least one of the first sensor unit or remote second sensor unit, according to the identified sensing modes thereof.

According to some embodiments, the sensors of the first and second sensor units are configured for sensing at least one of: respiration related movements of the individual, blood pressure and/or pulse related movements of the individual, the control unit further being configured for processing the sensors data for identifying alarming respiratory, blood pressure and/or pulse related situations, and the at least one output device being further configured for outputting alarms upon identification of alarming situations.

Optionally, each sensor of the first sensor unit and the remote second sensor unit comprises at least one piezoelectric transducer.

The remote second sensor unit may be configured for being placed and operated over a support of a bed or other resting furniture upon which the individual is to be rested for monitoring the individual while he/she is resting thereover.

According to some embodiments, the portable monitoring device is further configured for docking in a docking apparatus configured at least for holding thereof. For example, the docking apparatus may be configured to attach to resting furniture such as to allow placing the portable monitoring device therein.

According to some embodiments, the docking apparatus is further configured for communicating the second sensor unit with the portable monitoring device via a communication cable connectable thereto.

According to other embodiments, the communication between the portable monitoring device and the at least one remote second sensor is carried out via a wireless communication link such as yet not limited to radio frequency (RF) based communication, optical communication or ultrasound communication.

According to some embodiments, the portable monitoring device is adapted to sense when it is docked in the docking apparatus and automatically process only signal data arriving from the remote second sensor unit, until the second sensor unit is turned off and/or until the device is removed from the docking apparatus.

The carrying mechanism optionally comprises one of: a clip design configured for attaching the device over the individual's garment; a bracelet or necklace configured for carrying the device over the individual's wrist, leg or neck; a head wear.

The present disclosure further provides embodiments of a system for monitoring at least physical parameter for an individual, comprising: (i) a portable monitoring device being configured for being worn by the individual, the portable monitoring device comprising: a power source; a first sensor unit comprising at least one sensor for sensing at least one physical parameter of the individual; a control unit configured for receiving output signal data from the first sensor unit and from at least one other remote second sensor unit having at least one sensor for monitoring at least one physical parameter, identifying sensing mode of each of the first and second sensor units, and for processing data received from the first and/or second sensor unit; a carrying mechanism for having the portable monitoring device carried by the individual to be monitored, the control unit and the at first sensor unit being embedded in the carrying mechanism; and at least one output device for outputting indication and/or information associated with the processed data; and (ii) at least one remote non-portable second sensor unit comprising at least one sensor for sensing at least one physical parameter of an individual, the remote second sensor unit. The portable monitoring device is further configured for processing signal data of one of the first sensor unit or remote second sensor unit, according to an identified sensing mode indicative of which of the first sensor or second sensor units is currently being used for monitoring the individual therefrom.

According to some embodiments, the system further comprises a docking apparatus for holding the portable monitoring device thereby, wherein the at least one remote second sensor unit is configured for being placed over a support of a rest furniture for monitoring the individual when the individual is rested thereover, and wherein the docking apparatus is further configured for connecting the portable monitoring device to the at least one second sensor unit for receiving data therefrom.

The control unit of the portable monitoring device optionally comprises at least one processor for data processing and at least one communication unit for communicating with the first sensor unit and the at least one remote second sensor unit through at least one communication link.

According to some embodiments, the at least one parameter sensed by the sensors of the first and second sensor units and processed by the control unit is at least one of: respiration related movements, pulse and/or blood pressure, the processing unit further being configured for identifying alarming situations and output alarms upon identification of alarming situations through he at least one output device.

The present disclosure also provides embodiments of a system for monitoring at least one physical of an individual, comprising: (i) a portable monitoring device comprising: a first sensor unit having at least one sensor for sensing at least one physical parameter of the individual; a carrying mechanism configured for carrying the portable monitoring; a control unit configured for receiving output signal data from the first sensor unit and from another remote second sensor unit having at least one sensor for monitoring at least one physical parameter, identifying sensing mode of each of the first and second sensor units, and for processing data received from the first or second sensor units, according to the sensing modes thereof; and at least one output device for outputting indication and/or information associated with the processed first sensor and/or second sensor data; and (ii) a docking apparatus having a housing configured for holding the portable monitoring device therein, the docking apparatus being configured to connect with the at least one second sensor for communicating the portable device with the second sensor.

The present disclosure further provides embodiments of a system for monitoring at least respiration of an individual, the system comprising: (i) a portable monitoring device being configured for being worn over an individual's garment for portability thereof such as to monitor at least respiration of the individual by having at least one first sensor thereof sense at least one parameter indicative of respiration of the individual, for detection of at least respiration related alarming situations and outputting alerts upon detection of an alarming situation, the portable monitoring device further comprising a control unit for data communication, data processing and control of an output device for initiating and outputting alarms; (ii) at least one second sensor which is not configured to be worn by the individual, the at least one second sensor being configured to sense at least respiratory of the individual when in proximity thereto; and (iii) a docking device having a housing configured for holding the portable monitoring device therein and a second control unit for receiving data at least from the at least one second sensor, processing the received data, identifying alarming situations and initiating an alert upon identification of an alarming situation.

According to some embodiments, at least one of: the portable monitoring device and/or the docking device comprises at least one output device for outputting alarms upon identification of an alarming situation by the control unit of the portable monitoring device and/or by the control unit of the docking device.

The present disclosure further provides embodiments of a method for monitoring at least one physical parameter for an individual comprising: identifying sensing mode of a portable monitoring device having a first sensor unit configured for sensing at least one physical parameter of an individual when carrying the device and of a remote second sensor unit over which the individual can be rested configured for sensing the at least one physical parameter; receiving and processing data from one of the portable monitoring device or remote sensor unit according to the identified sensing mode thereof, for allowing processing only data from the sensor unit of the device being used; and outputting indication and/or information associated with the processed data.

According to some embodiments, the identification of the sensing mode of each of the portable monitoring device and second sensor unit is carried out automatically by sensing whether the portable monitoring device is docked in a docking apparatus or not, whereas once the portable monitoring device is docked at the docking apparatus only data from the remote sensor unit is processed and if the portable monitoring device is not docking at the docking apparatus only data from the portable monitoring device first sensor unit is processed.

Optionally, the data processing is adapted for detection of at least one alarming situation, wherein the method further comprises operating an alarm once an alarming situation is detected.

According to some embodiments, the processing and outputting is carried out using a processor and output means of the portable monitoring device.

The at least one physical parameter being sensed or deduced comprises at least one of: respiratory related movements, pule related movement, blood pressure related movements, wherein said first and second sensor units each comprises at least one movement sensor.

According to some embodiments, the first and second sensor units are adapted to send data to a control unit of said portable monitoring device for data processing via at least one communication link.

The method optionally further comprises transmitting data associated with the processed data to at least one other remote communication device such as a mobile device (e.g. smartphone) of a caretaker of the individual being monitored.

BRIEF DESCRIPTION OF THE DRAWINGS

FIG. 1A shows a rearward isometric view of the system in a monitoring state in which the portable device is docked at the docking apparatus; and FIG. 1B shows a rearward view of the system in a monitoring state in which the portable device is docked at the docking apparatus.

DETAILED DESCRIPTION

Figure 1A:
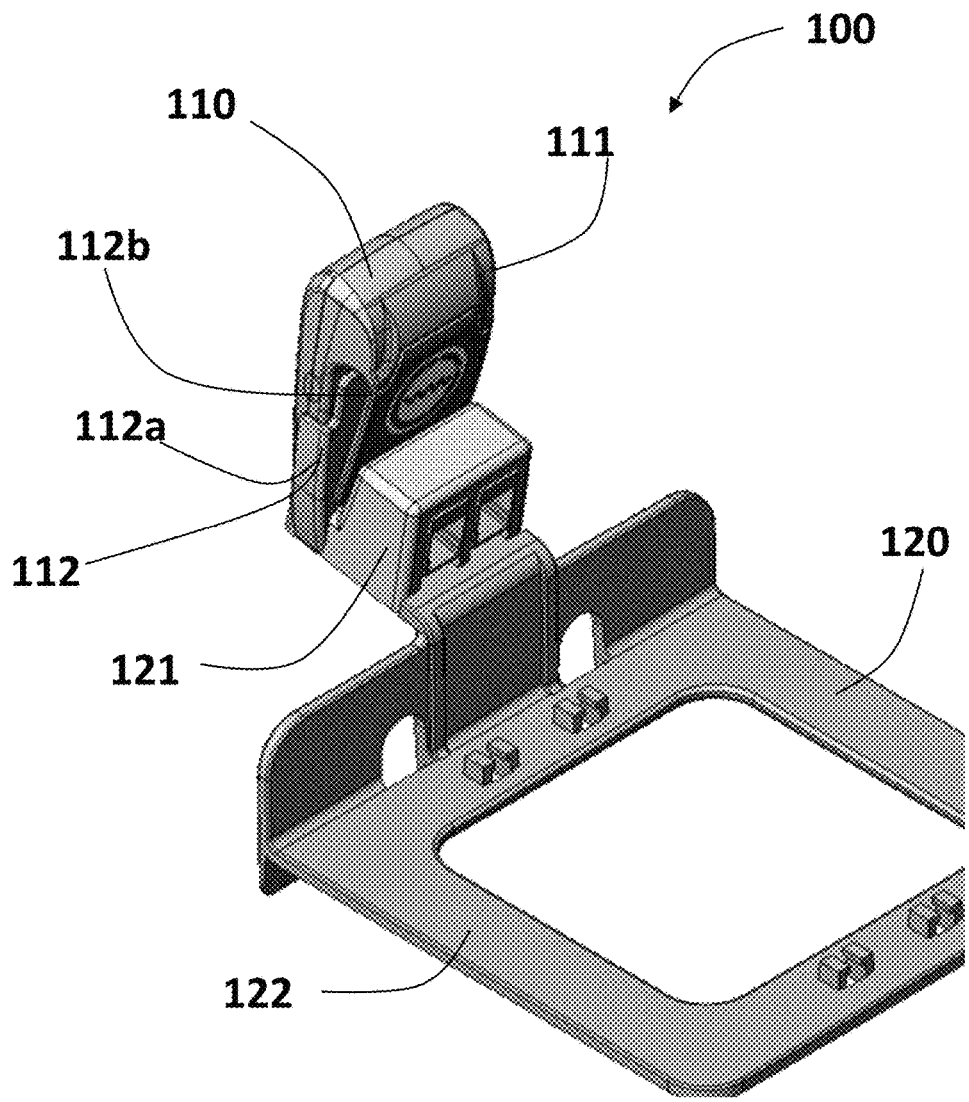
FIGS. 1A and 1B show a system for monitoring an individual having a portable monitoring device designed for being attached to the individual's garment and a docking apparatus designed for attaching to resting furniture, for connecting to a remote sensor unit and for docking the portable monitoring device thereto, according to some embodiments of the present invention.

In the following detailed description of various embodiments, reference is made to the accompanying drawings that form a part thereof, and in which are shown by way of illustration specific embodiments in which the disclosed embodiments may be practiced. It is understood that other embodiments may be utilized and structural changes may be made without departing from the scope of the disclosure.

The present disclosure provides embodiments of portable devices, systems and methods using thereof for monitoring at least one physical parameter of an individual such as respiration, heartbeat, blood pressure and the like. According to some embodiments, the portable monitoring device comprises: a first sensor unit having one or more sensors such as a piezoelectric transducer movement sensor for sensing the physical parameter of the individual; a control unit configured for receiving data from the first sensor unit and optionally also from at least one other remote second sensor unit having a sensor for monitoring at least one physical parameter, identifying sensing mode of each of the first and second sensor units, and processing the received data; a carrying mechanism for having the portable device carried by the individual to be monitored; and one or more output devices for outputting indication and/or information associated with the processed data. The control unit is configured for processing signal data of the first sensor unit or the remote second sensor unit, according to the identified sensing modes thereof.

For example, if the first sensor unit embedded in the portable monitoring device is switched off or switched to a sleep mode, the control unit will automatically process data received from the second remote sensor unit and vice versa.

In some embodiments, the system comprises one or more docking apparatuses for docking the portable device thereto or therein for automatic switching to monitoring the individual with the second remote sensor unit. This is done, for example, for individuals such as yet not limited to, babies or toddlers which may carry the portable monitoring device over their body such as by clipping to their garment or dipper or by wearing the device as a bracelet, during their active waking hours and when they are put to bed the device can be docked to the docking apparatus switching to monitoring the individual through the remote sensor unit placed under their bed mattress. The portable monitoring device may be connectable to remote sensor unit via the docking apparatus requiring not rewiring of the remote sensor unit. In this way the switching from the portable monitoring device to the stationary remote second sensor unit can be done automatically by having the control unit "sense" the docking of the device. The docking sensing can be achieved by enabling electrical connection between an input node of the portable monitoring device to a cable connected through the docking apparatus also connecting to the second sensor unit at its other end.

According to some embodiments, the actual docking of the portable monitoring device will automatically turn the first sensor unit off or switch it to a sleep mode requiring less battery power and receive and process only data that arrives from the remote second sensor unit. In this way the identification of the operation mode of the sensor units is automatically done by sensing the connecting to the second sensing unit.

The carrying mechanism may include a housing and an attachment mechanism such as a clip configured for attaching the device to the individual's garment or a wearable device or artifact such as a bracelet, necklace or headwear.

The control unit may be a microprocessor unit with communication means enabling communicating with the first and second sensor units through one or more communication technologies and/or links such as through cable communication, wireless communication such as radio frequency (RF) based communication, infrared (IR) based communication ultrasonic based communication and the like, using one or more communication protocols.

The one or more sensors in each communication unit may include transducers such as piezoelectric crystal sensors for sensing minute movements or any other known in the art sensors that can be used for detection/extraction of one or more vital signs related parameters therefrom such as respiration behavior, pulse, blood pressure, sweating, shivering and the like.

In case of sensing at least respiratory behavior of the individual, the data from the sensors of the first and second sensor units may be processed to identify the respiratory behavior to identify alarming situations relating thereto such as apnea, irregular breathing, slow and fast breathing and the like. Upon identification of an alarming situation an alarm set at the portable monitoring device may be operated for alerting the individual and/or caretakers thereof.

The portable monitoring device may also have an indication lamp for indicating the operational mode of the device such for indicating that the device is operated, its sleep mode if exist and battery state.

The device may be operable via an embedded power source such as a battery.

According to some embodiments the system comprises the portable monitoring device, the docking apparatus and the remote second sensor unit as a whole pack for monitoring the individual when actively awake and when sleeping.

Figure 1B:
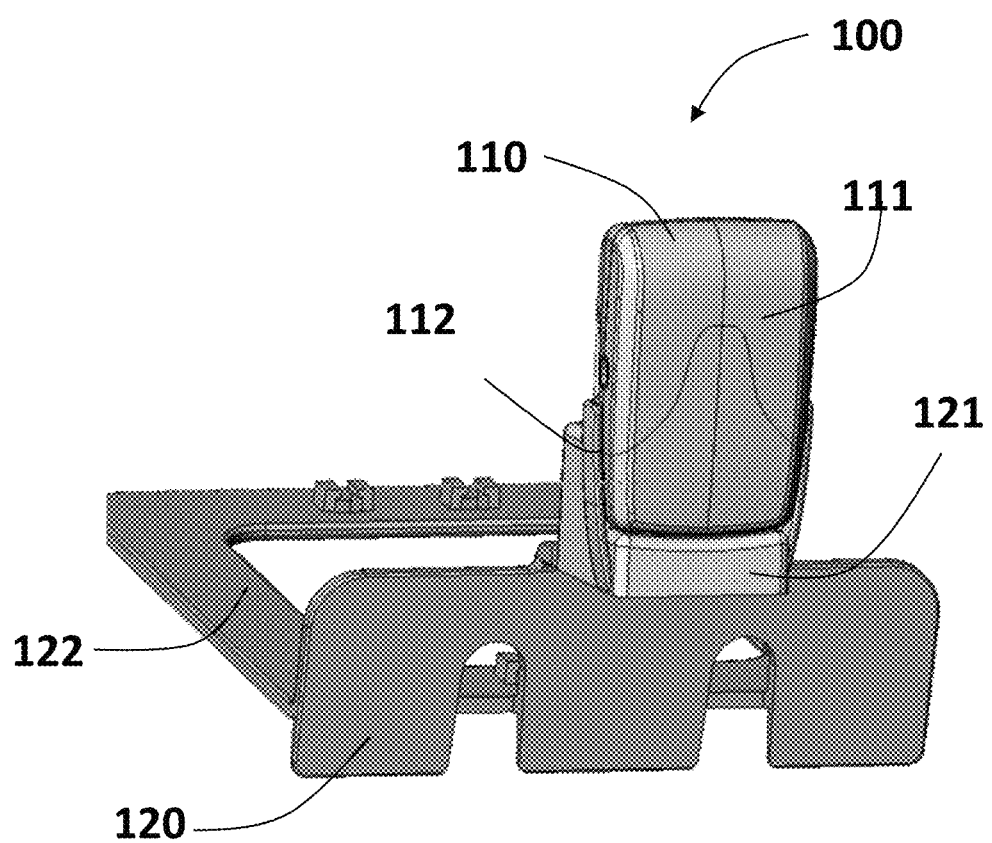

Reference is now made to FIGS. 1A and 1B show a system 100 for monitoring an individual such as an elder person, an ill person requiring respiratory or other monitoring, a baby or a toddler and the like, according to some embodiments of the invention. The system 100 has a portable monitoring device 110 designed for being attached to the individual's garment; and a docking apparatus 120 designed for attaching to resting furniture, for connecting to a remote sensor unit and for docking the portable monitoring device 110 thereto, according to some embodiments of the present invention. The system may also include one or more remote second sensor units (not shown).

The potable monitoring device 10 includes a clip member 112 having a housing 111 and clips 112a and 112b configured for attaching the device 110 to a garment such as dipper or trousers of the individuals, such that the sensor of the first sensor unit thereof (not shown) will be in proximity or in contact with the individual's body or garment e.g. for sensing movements thereof indicative of the individual's breathing and/or pulse.

The docking apparatus 120 has a docking member 121 configured for holding thereby the monitoring device 110 and optionally a connecting member 122 for connecting thereof to a bed or any other rest furniture for having the control unit (not shown) of the device 110 monitor the individual when sleeping or resting thereover by receiving data from a remote second sensing unit positioned under a support of the rest furniture.

Figure 2:
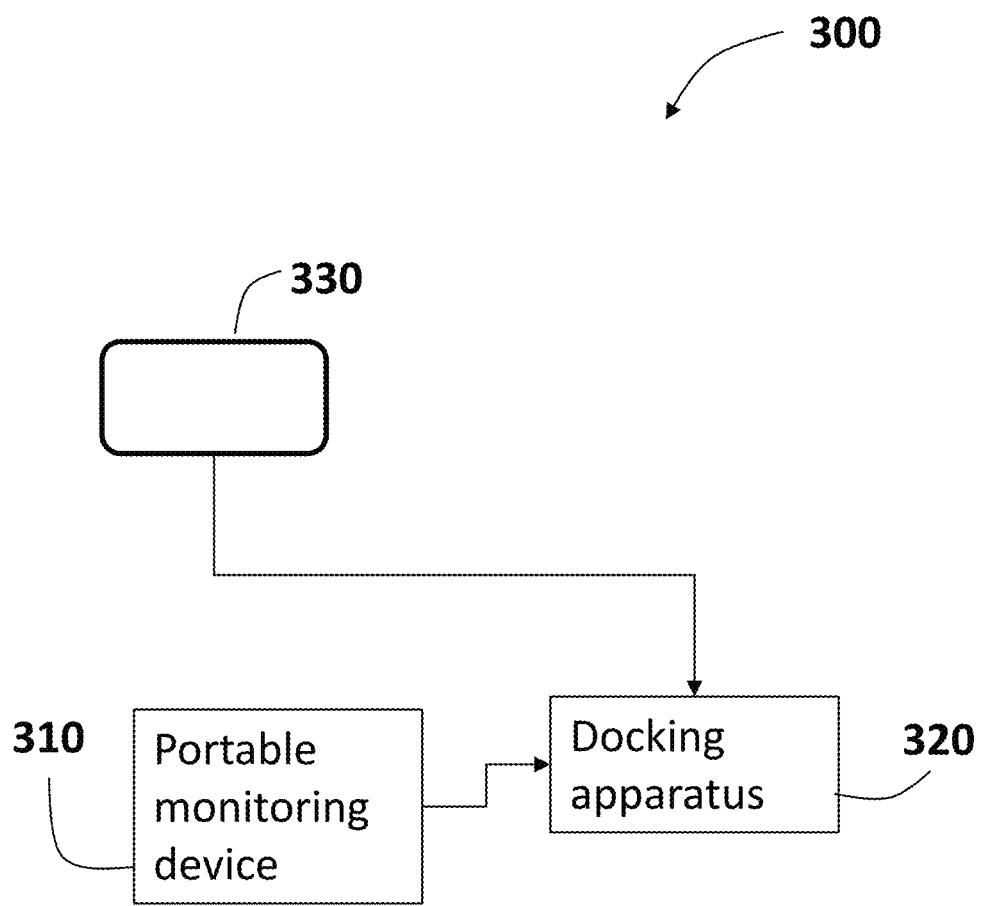
FIG. 2 shows a block diagram of a system for monitoring an individual, in which the second sensor unit connects to the portable monitoring device via the docking apparatus, according to other embodiments of the invention.

Reference is now made to FIG. 2, showing a block diagram of a system 200 comprising a portable monitoring device 210 configured for monitoring at least one physical parameter of the individual carrying thereof; a docking apparatus 220 for docking the portable monitoring device 210 thereto; and a second sensing unit 230 positioned under a support of a rest furniture for sensing the same one or more physical parameters while the individual is rested over the furniture.

The docking apparatus 220 allows easy and quick connecting of the second sensor unit 230 to the portable monitoring device 210 when docking thereto, by having for instance, an output connector of a communication cable extended from the second sensing unit 230 is connected to an inlet holder of the docking apparatus 220 such that once the portable monitoring device 210 is docked in the docking apparatus 220, the output connector is inserted to in contact with an inlet node of the portable monitoring device 210 thereby automatically connecting thereof to the second sensor unit 230.

According to some embodiments, the docking apparatus is a simple holder of the portable monitoring device 210 and only allows physically connecting the second sensor unit 230 thereto.

According to other embodiments, the docking apparatus 220 also includes indication means for indicating that the docking is done correctly i.e. that the second sensor unit 230 connects to the portable monitoring device 210 and optionally also includes a processor and communication means for processing the data from the second sensor unit 230 thereover for simply sending the portable monitoring device 210 alert messages data for outputting alert when an alarming situation is detected in the processing of the sensor data from the second sensor unit 230. The data processing and decision making may alternatively be carried out at the second sensor data 230 only transmitting alert data when detecting an alarming situation such as no movement (indicative of possible apnea for respiratory monitoring or no pulse etc.).

Figure 3:
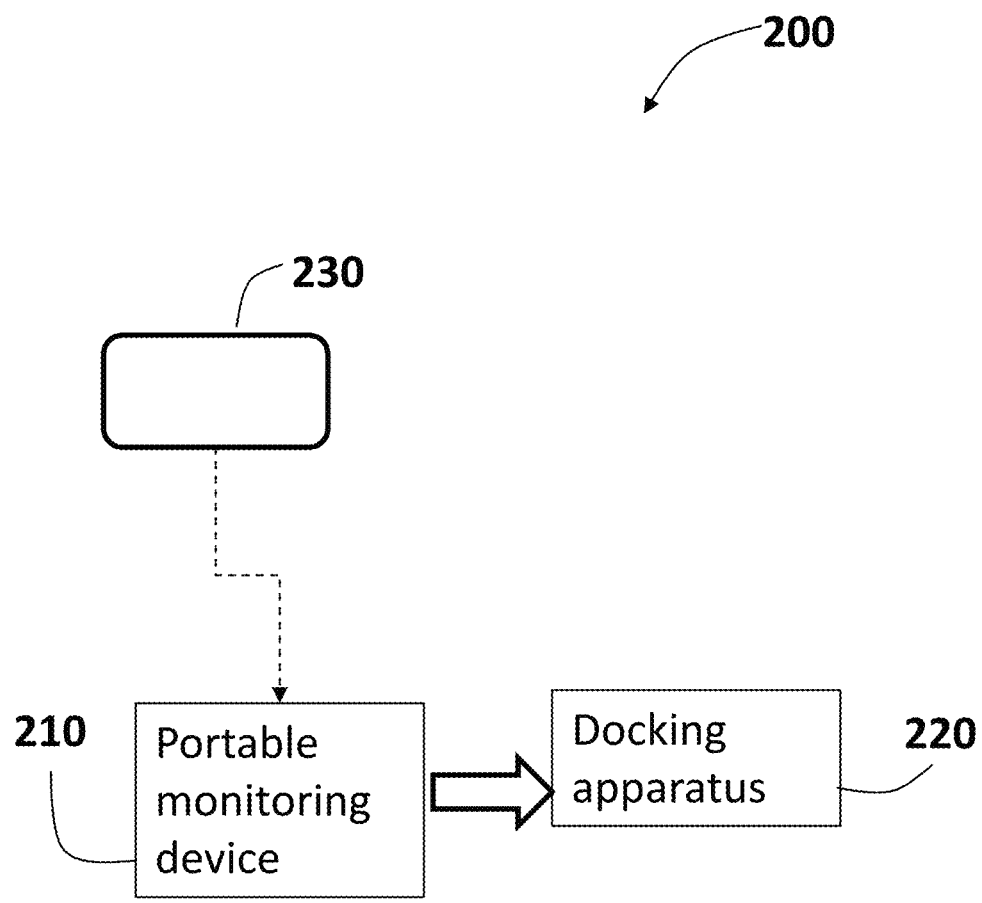
FIG. 3 shows a block diagram of a system for monitoring an individual, in which the second sensor unit directly connects to the portable monitoring device, according to other embodiments of the invention.

Reference is now made to FIG. 3, showing a block diagram of a system 300 comprising a portable monitoring device 310 configured for monitoring at least one physical parameter of the individual carrying thereof; a docking apparatus 320 for docking the portable monitoring device 310 thereto; and a second sensing unit 330 positioned under a support of a rest furniture for sensing the same one or more physical parameters while the individual is rested over the furniture. In this case, the second sensor unit 330 is directly connectable to the portable monitoring device 310.

Figure 4:
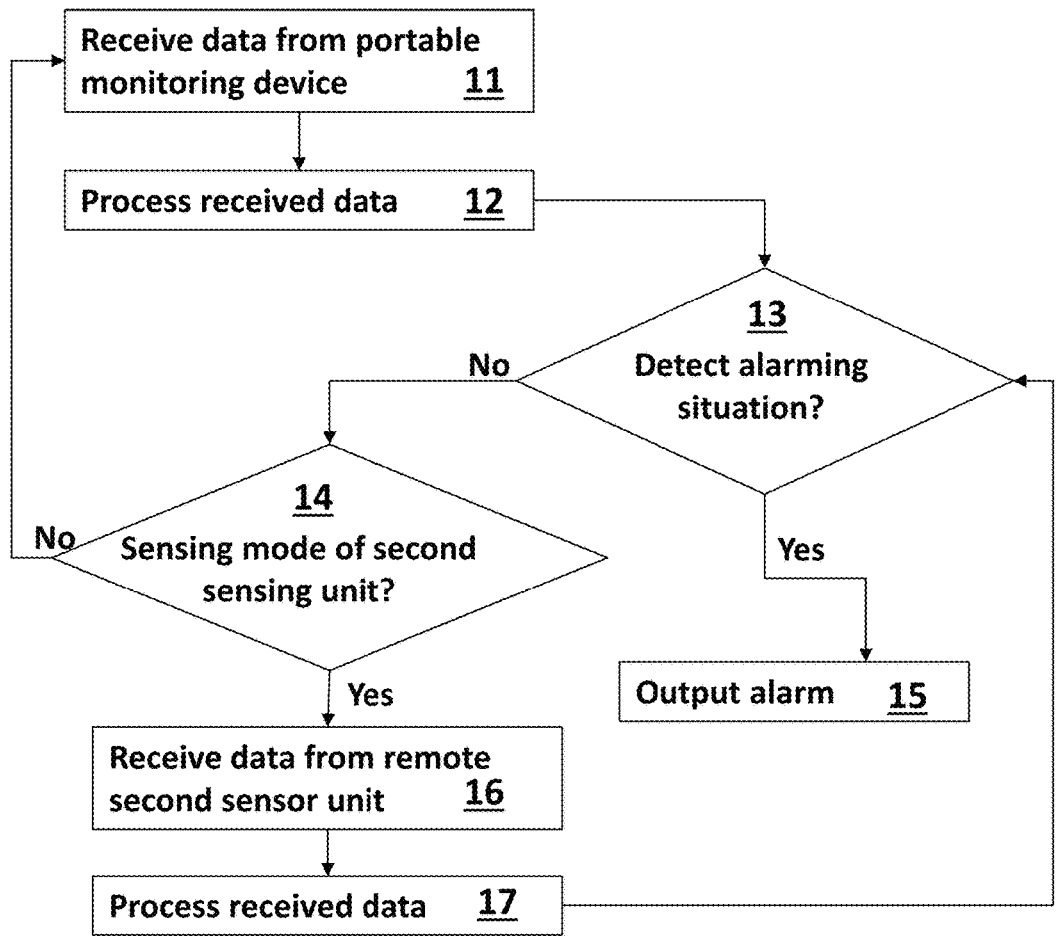
FIG. 4 shows a flowchart schematically illustrating a process of monitoring an individual, according to some embodiments of the invention

Reference is now made to FIG. 4 which is a flowchart schematically illustrating a process of monitoring an individual, according to some embodiments of the invention, using the above described system or some embodiments thereof.

The method includes identifying the sensing mode of each of the first sensor unit of the portable monitoring device and the remote second sensor unit 14 and receive and process data only from the sensor unit being used, i.e. from the portable monitoring device i.e. steps 11-12 or from the remote second sensor unit i.e. steps 16-17, for detecting alarming situations 13 and initiating an alarm outputting 15 upon such detection.

The processing of the data from each of the sensor units and the outputting of the alarms and optionally other information relating to the processed sensors data may all be carried out at the portable monitoring device or at least additionally also at a remote device such as at one or more mobile devices of a caretaker of the monitored individual by having the portable device being adapted to send data to those remote devices.

According to some embodiments of the invention, the portable monitoring device includes visual output means enabling for instance to display measured data such as the pulse rate, breathing rate (number of inhalations per minute) and the like and also an alarming situation indication when such is detected by the processing of the sensor data.

Many alterations and modifications may be made by those having ordinary skill in the art without departing from the spirit and scope of the disclosure. Therefore, it must be understood that the illustrated embodiments have been set forth only for the purposes of examples and that they should not be taken as limiting the disclosure as defined by the foregoing and its various embodiments and/or by the following claims. For example, notwithstanding the fact that the elements of a claim are set forth below in a certain combination, it must be expressly understood that the disclosure includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element is explicitly contemplated as within the scope of the disclosure.

The words used in this specification to describe the various disclosed embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub-combination or variation of a sub-combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, and what can be obviously substituted.

Although various embodiments have been described in detail, nevertheless changes and modifications, which do not depart from the teachings of the present disclosure, will be evident to those skilled in the art. Such changes and modifications are deemed to come within the purview of the disclosure and the appended claims.

The invention claimed is:

1. A method for monitoring at least one physical parameter for an individual, said method comprising:
   Identifying a sensing mode of a portable monitoring device including a first sensor unit configured for sensing at least one physical parameter of an individual when carrying the portable monitoring device and of a remote second sensor unit over which the individual can be rested configured for sensing the at least one physical parameter;
   receiving and processing data from one of the portable monitoring device or the remote second sensor unit according to the identified sensing mode, for processing only data from either the first sensor unit or the remote second sensor unit; and
   outputting an indication and/or information associated with the processed data, wherein the identification of the sensing mode of each of the portable monitoring device and the remote second sensor unit is carried out automatically by sensing whether the portable monitoring device is docked in a docking apparatus or not, whereas once the portable monitoring device is docked at the docking apparatus only data from the remote second sensor unit is processed and if the portable monitoring device is not docked at the docking apparatus only data from the portable monitoring device including the first sensor unit is processed.

2. The method according to claim 1, wherein said processing is adapted for detection of at least one alarming situation, wherein said method further comprises operating an alarm once an alarming situation is detected.

3. The method according to claim 1, wherein said processing and outputting is carried out using a processor and an output means of the portable monitoring device.

4. The method according to claim 1, wherein the at least one physical parameter comprises at least one of: respiratory related movements, pule related movement, blood pressure related movements, wherein said first sensor unit and said remote second sensor unit each comprise at least one movement sensor.

5. The method according to claim 1, wherein said first sensor unit and said remote second sensor unit are adapted to send data to a control unit of said portable monitoring device for data processing via at least one communication link.

6. The method according to claim 1, further comprising transmitting data associated with the processed data to at least one other remote communication device.

7. The method according to claim 1, wherein each sensor of said first sensor unit and said remote second sensor unit comprises at least one piezoelectric transducer.

8. The method according to claim 1, wherein said remote second sensor unit is configured for being placed and operated over a support of a bed or other resting furniture upon which the individual is to be rested for monitoring the individual while he/she is resting thereover.

9. The method according to claim 1, wherein said docking apparatus is configured to attach to resting furniture such as to allow placing said portable monitoring device therein.

10. The method according to claim 1, wherein said docking apparatus is further configured for communicating said remote second sensor unit with said portable monitoring device via a communication cable connectable thereto.

11. The method according to claim 1, wherein the communication between said portable monitoring device and said at least one remote second sensor unit is carried out via a wireless communication link.

12. The method according to claim 11, wherein said wireless communication link is based on radio frequency (RF) communication, optical communication or ultrasound communication.

13. The method according to claim 1, wherein said portable monitoring device is carried via carrying mechanism comprising one of: a clip design configured for attaching said portable monitoring device over the individual's garment; a bracelet or necklace configured for carrying said portable monitoring device over the individual's wrist, leg or neck; or a head wear.

14. A computing system comprising: at least one processor; and at least one memory communicatively coupled to the at least one processor, the at least one memory storing computer-readable instructions that, when executed by the at least one processor, cause the computing system to implement a method of recommending video content, the method comprising:
   identifying a sensing mode of a portable monitoring device having a first sensor unit configured for sensing at least one physical parameter of an individual when carrying the device and of a remote second sensor unit over which the individual can be rested configured for sensing the at least one physical parameter;
   receiving and processing data from one of the portable monitoring device or remote sensor unit according to the identified sensing mode thereof, for allowing processing only data from the sensor unit being used; and outputting indication and/or information associated with the processed data, wherein the identification of the sensing mode of each of the portable monitoring device and the remote second sensor unit is carried out automatically by sensing whether the portable monitoring device is docked in a docking apparatus or not, whereas once the portable monitoring device is docked at the docking apparatus only data from the remote sensor unit is processed and if the portable monitoring device is not docking at the docking apparatus only data from the portable monitoring device first sensor unit is processed.

15. The system according to claim 14, wherein said processing is adapted for detection of at least one alarming situation, wherein said method further comprises operating an alarm once an alarming situation is detected.

16. The system according to claim 14, wherein said processing and outputting is carried out using a processor and an output means of the portable monitoring device.

17. The system according to claim 14, wherein the at least one physical parameter comprises at least one of: respiratory related movements, pule related movement, blood pressure related movements, wherein said first sensor unit and said remote second sensor unit each comprise at least one movement sensor.

18. The system according to claim 14, wherein said first sensor unit and said remote second sensor unit are adapted to send data to a control unit of said portable monitoring device for data processing via at least one communication link.

19. The system according to claim 14, further comprising transmitting data associated with the processed data to at least one other remote communication device.

20. The system according to claim 14, wherein each sensor of said first sensor unit and said remote second sensor unit comprises at least one piezoelectric transducer.

21. The system according to claim 14, wherein said remote second sensor unit is configured for being placed and operated over a support of a bed or other resting furniture upon which the individual is to be rested for monitoring the individual while he/she is resting thereover.

22. The system according to claim 14, wherein said docking apparatus is configured to attach to resting furniture such as to allow placing said portable monitoring device therein.

23. The system according to claim 14, wherein said docking apparatus is further configured for communicating said remote second sensor unit with said portable monitoring device via a communication cable connectable thereto.

24. The system according to claim 14, wherein the communication between said portable monitoring device and said at least one remote second sensor unit is carried out via a wireless communication link.

25. The system according to claim 24, wherein said wireless communication link is based on radio frequency (RF) communication, optical communication or ultrasound communication.

26. The system according to claim 14, wherein said portable monitoring device is carried via carrying mechanism comprising one of: a clip design configured for attaching said portable monitoring device over the individual's garment; a bracelet or necklace configured for carrying said portable monitoring device over the individual's wrist, leg or neck; or a head wear.

* * * * *